United States Patent [19]

Faasse, Jr.

[11] Patent Number: 4,556,441
[45] Date of Patent: Dec. 3, 1985

[54] PHARMACEUTICAL PACKAGING METHOD

[76] Inventor: Adrian L. Faasse, Jr., 4908 Stauffer Ave., SE., Kentwood, Mich. 49508

[21] Appl. No.: 460,582

[22] Filed: Jan. 24, 1983

[51] Int. Cl.$^4$ .................... B32B 31/00; B32B 31/18
[52] U.S. Cl. .................................. 156/247; 128/114; 128/156; 156/248; 156/249; 156/256; 156/264; 156/265; 156/267; 156/268; 604/364; 604/897
[58] Field of Search ............... 156/247, 248, 249, 250, 156/256, 264, 265, 267, 268, 164; 604/364, 896, 897; 128/114, 156

[56] References Cited

U.S. PATENT DOCUMENTS

| | | | |
|---|---|---|---|
| 2,703,083 | 3/1955 | Gross | 156/248 |
| 2,862,846 | 12/1958 | Blackford et al. | 156/249 |
| 3,834,963 | 9/1974 | Hoffman | 156/256 |
| 4,117,841 | 10/1978 | Perrotta et al. | 604/897 |
| 4,306,928 | 12/1981 | Okui | 156/267 |
| 4,341,208 | 7/1982 | Gordon | 604/897 |
| 4,364,787 | 12/1982 | Radzins | 156/164 |
| 4,374,691 | 2/1983 | Van Den Bergh | 156/247 |

*Primary Examiner*—Jay H. Woo
*Assistant Examiner*—Timothy W. Heitbrink
*Attorney, Agent, or Firm*—Price, Heneveld, Huizenga & Cooper

[57] ABSTRACT

A machine and method for making base assemblies for medicine dispensing compresses, includes using a web of substantially imperforate material, and a web of backing material having a base layer with an adhesive on one side to attach the compress to the skin of the user. A plurality of individual foil lids or dam patches are cut from the web of imperforate material, and applied to the adhesive side of the base layer. A release or cover layer is applied to the adhesive side of the base layer to sandwich the dam patches between the base layer and the cover layer. Individual base units are cut into the base layer, with one of the dam patches positioned within each of the base units. Apertures are cut in the areas of the cover layer overlying the dam patches to access a portion of the foil surface of each of the dam patches. The offal portion of the base layer is removed from the cover layer, forming fabricated base assemblies for the compresses, which are conveniently carried together on the cover layer for final assembly. The dam patch cutting and applying steps may include roller die cutting the web of imperforate material, separating the dam patches from the offal portion by a vacuum operated applicator drum, and pressing the cut dam patches into contact with the adhesive side of the base layer. For final assembly of the compresses, a medicine-filled pad is positioned on each of the dam patches, and an imperforate, removable outer sheet is applied over each of the medicine-filled pads to form sealed reservoirs in which the medicine-filled pads are retained.

29 Claims, 13 Drawing Figures

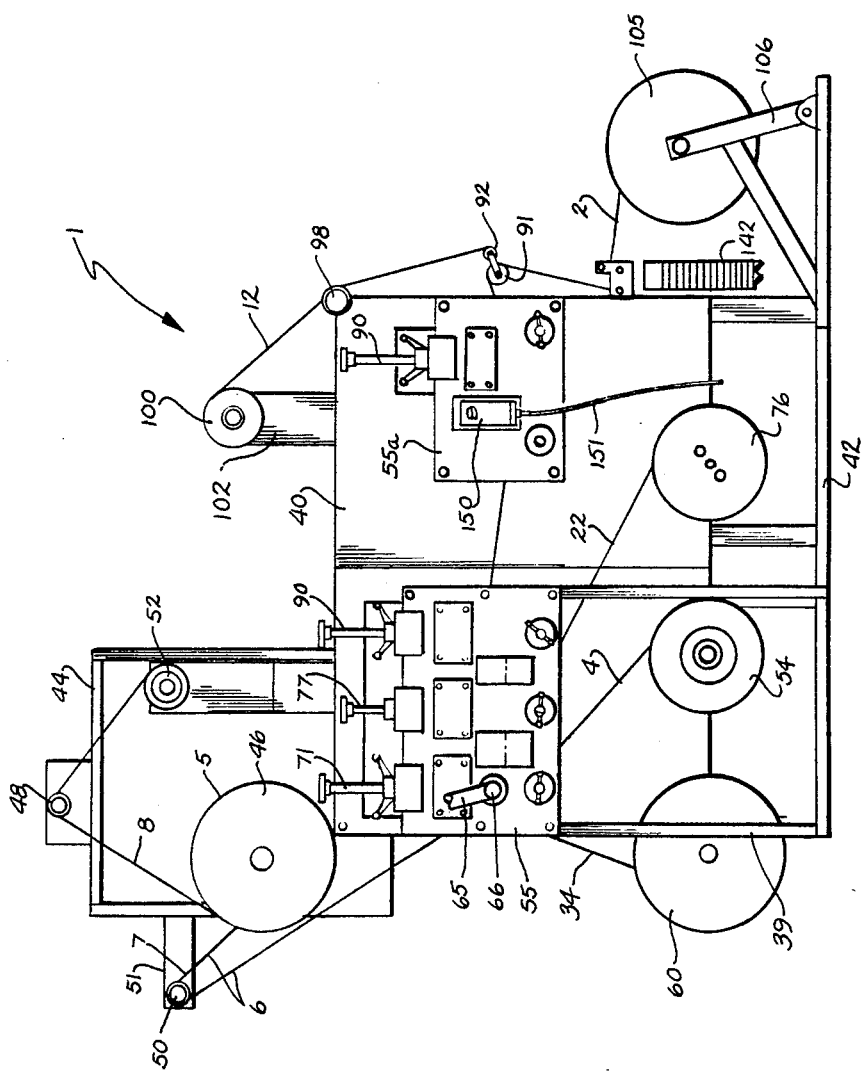

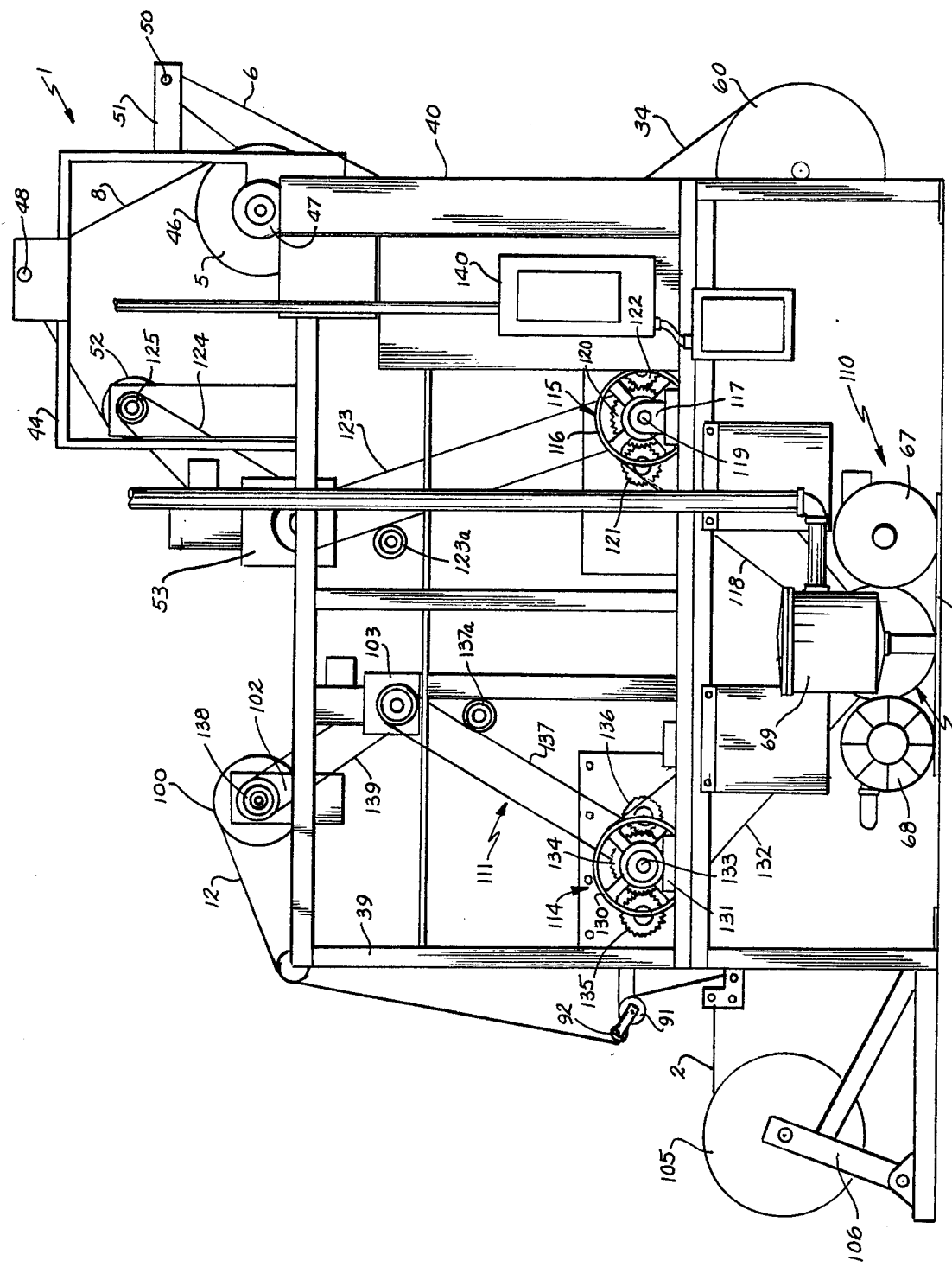

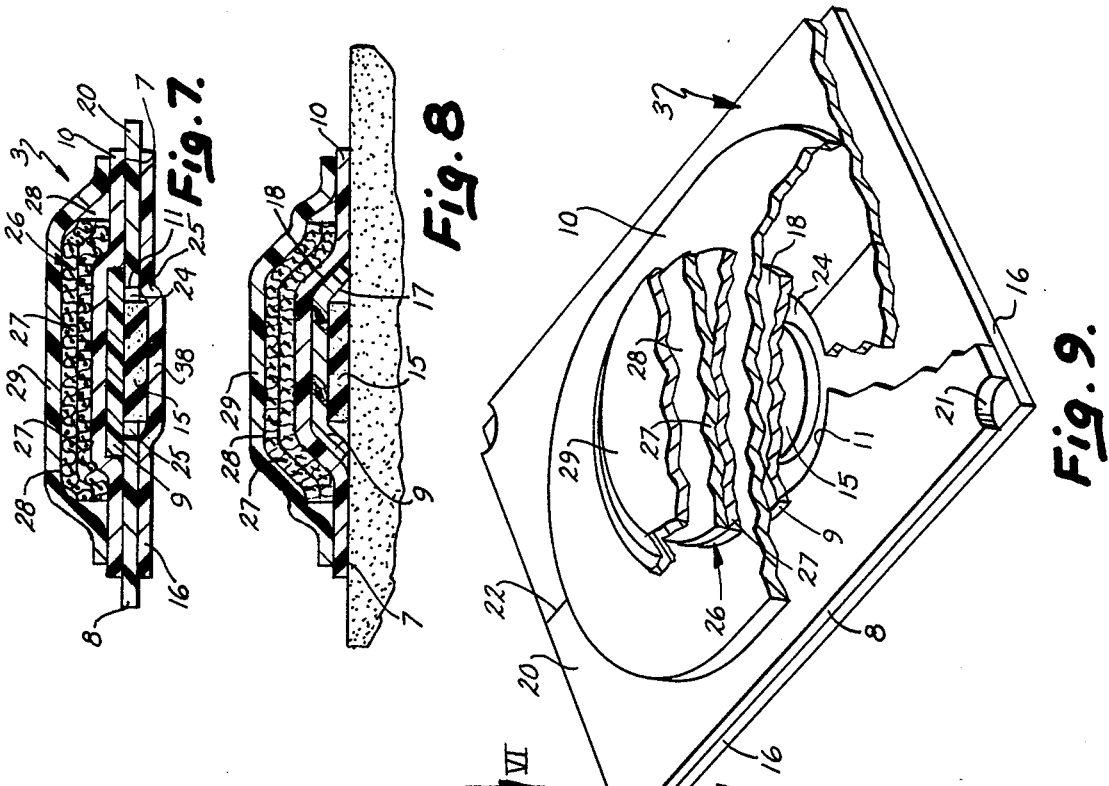
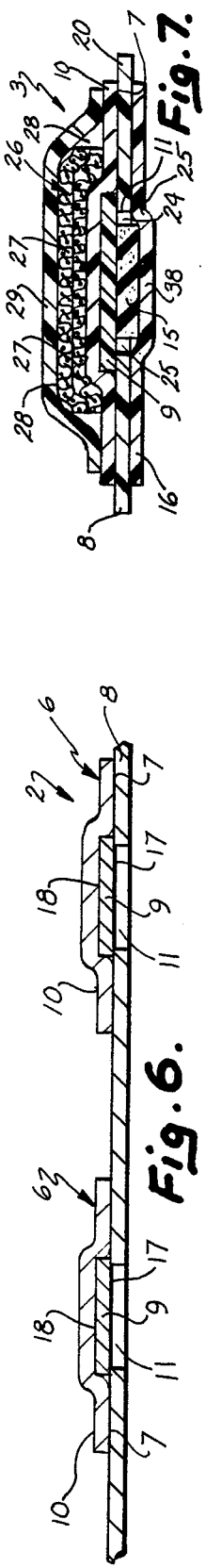
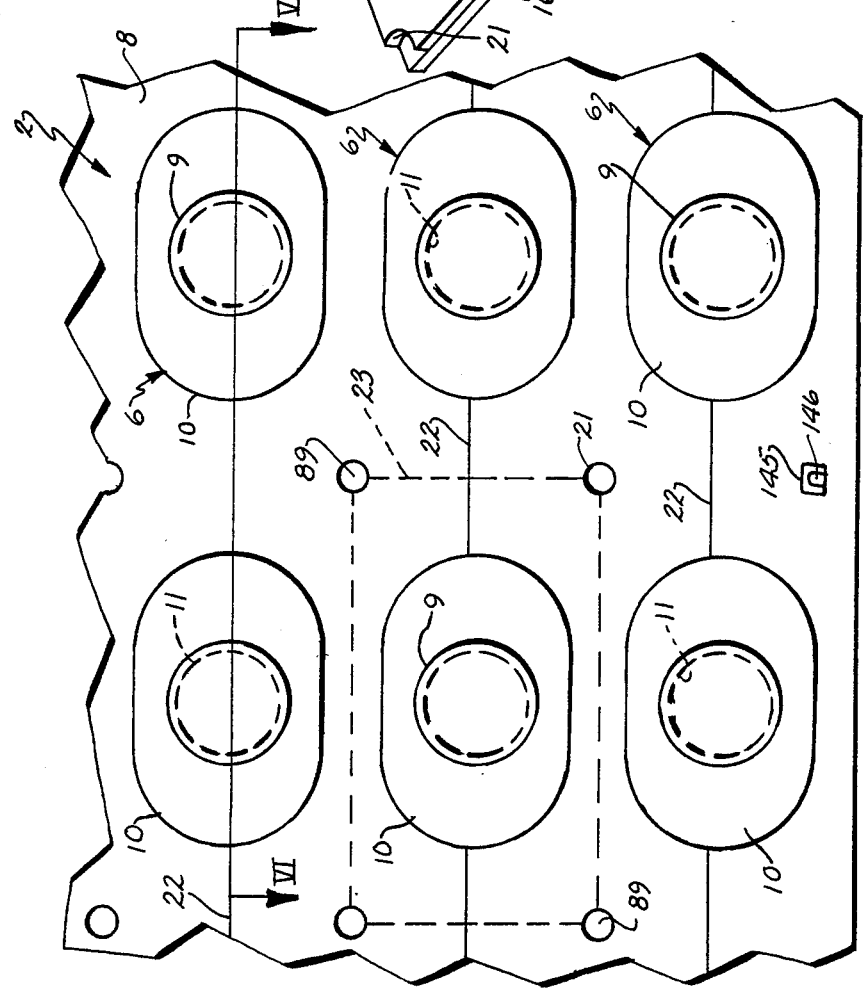

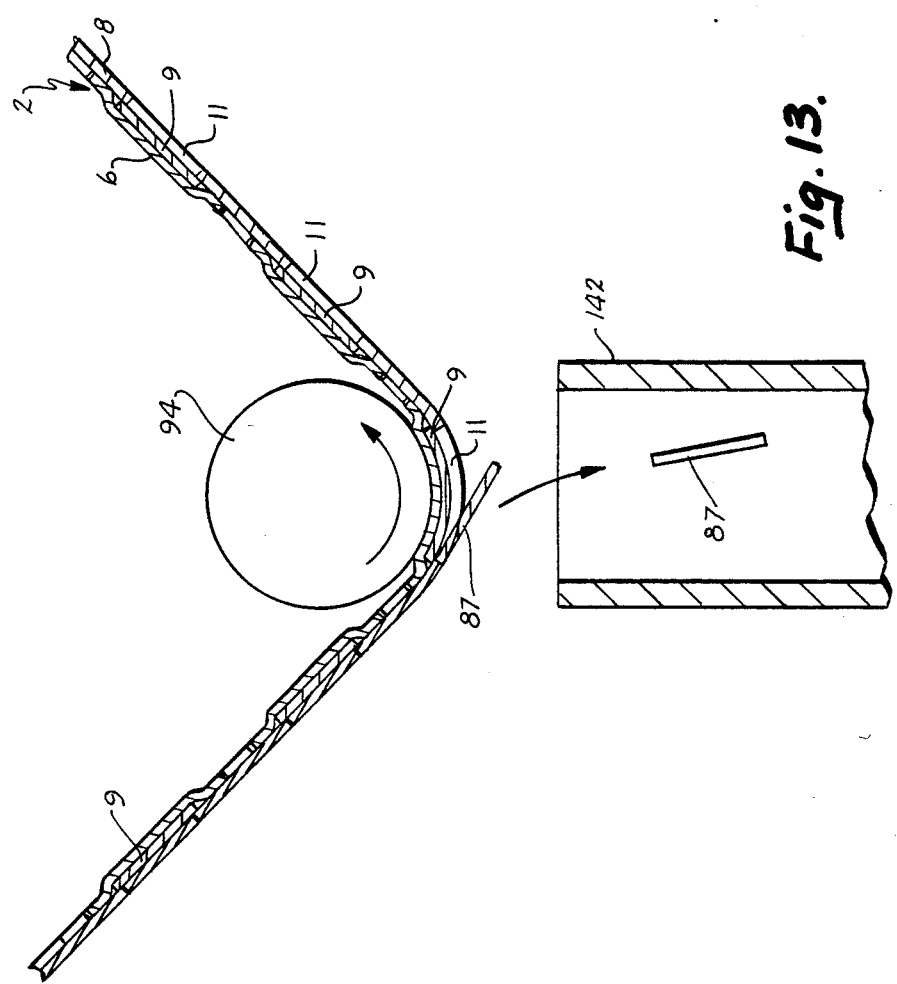

PHARMACEUTICAL PACKAGING METHOD

BACKGROUND OF THE INVENTION

Medications are administered to human patients in a wide variety of different ways. Normally, those medications which can be administered by the patient himself are in tablet or capsule form, and are taken orally and ingested into the patient's system. However, certain types of medications, such as nitroglycerin and the like, are applied topically, and are absorbed through the patient's skin for direct introduction into the patient's blood stream. Such medications are said to be introduced into the human body by "transdermal infusion" or "transdermal absorption."

Heretofore, transdermal infusion of naturally absorptive medications like nitroglycerin has been accomplished by placement of the nitroglycerin tablet under the patient's tongue. Although this type of process could be easily administered by the average patient himself, as opposed to hypodermic injections, the release time for the medication is rather fast, such that controlled, continuous flow of medication into the patient's system is not possible. Because the placement of a tablet under the user's tongue causes a distraction to everyday activities, this type of medicating procedure is typically limited to periodic requirements and/or emergency situations.

Another type of transdermal absorption medication developed is in the form of an ointment, which is applied topically, and includes a carrier, such as a petroleum base to provide a controlled release of the active ingredients. A predetermined dosage of the ointment is spread onto the patient's skin, such as the chest region, and the medication (i.e., nitroglycerin) is absorbed continuously into the systemic circulation. An applicator stick or paddle is normally used to apply the ointment to the patient, so that the medication is not inadvertently absorbed through the fingers of the person applying the medication. To insure that the medication is not accidently rubbed off of the patient's skin, a sheet of plastic film or wrap is placed over the medicated area, which is held in place by adhesive tape or the like. The plastic film also prevents the amount of the dosage from being disturbed, and protects the clothing of the patient. Since the ointment must be left on the patient's skin for relatively long periods of time, usually eight or more hours per day, it is important that the medication be isolated to the extent possible, so that the patient is able to carry out his normal, daily activities. However, skin movement around the adhesive tape tends to ruin the seal about the medication, as does bathing, swimming, exercise and other similar activities. Also, additional supplies of applicators, adhesive tape, and plastic film must be kept on hand at all times.

Very recently bandages or compresses have been developed to facilitate the application of transdermally absorbed medications. These compresses, such as the articles described hereinbelow, generally comprise a base assembly on which a medicated, gel-like disc or pad is supported. The compress is retained in a protective package for storage, and includes an adhesive arrangement to attach the medicated pad to the skin of the user, preferably at a location free of hair, such as the chest or inner arm. The compresses hold a predetermined dosage of medication, and are designed to be worn continuously (e.g., one unit per every 24 hour period), to achieve a slow, well-controlled rate of absorption into the patient's system. Heretofore, such compresses have been rather expensive, particularly for everyday use.

Presently, work is being conducted on the use of compresses to administer other types of drugs, which are not naturally transdermally absorbed, through the use of carrying agents such D.S.M.O. The convenience of application, and slow, controlled absorption rate achieved by a compress are also beneficial in these applications.

Since such compresses are prepackaged with an exact, preselected dosage of medication, it is extremely important that they be capable of securely storing the liquid medication for relatively long periods of time without leaking, or effecting the purity or potency of the medication. Also, it is very advantageous that such compresses can be opened and applied easily, and will not leak once in place, even during exercise, bathing, swimming, and other similar activities. Naturally, it is further desirable that the compresses have an uncomplicated construction, which can be quickly and economically manufactured.

SUMMARY OF THE INVENTION

A machine and method for economically making the base assemblies which hold the medicine dispensing compresses in place comprises providing a web of substantially imperforate material, and a web of backing material. The backing material has a base layer with means for adhering it to the skin of the user. A plurality of individual dam patches on which medicated pads are to be supported are cut from the web of imperforate material. The cut dam patches are applied to the adherent side of the base layer, so that the interior surfaces of the dam patches are oriented outwardly. A cover layer is applied over the base layer to sandwich the dam patches between the base layer and the cover layer. The base layer is then cut into individual base units, with one of the dam patches positioned within each base unit. A plurality of apertures are then cut in the cover layer and removed therefrom to selectively expose and access the interior foil surfaces of the dam patches on which the medicated pads are ultimately positioned. The offal portion of the base layer is removed from the cover layer, whereby the fabricated base assemblies for the compresses are carried conveniently together on the cover layer for final assembly.

The dam patch cutting and applying steps may include roller die cutting through the web of imperforate material, and temporarily attaching the dam patches to a rotating applicator drum. The offal portion of the imperforate material is separated from the cut dam patches on the rotating applicator drum, and the individual dam patches are then released from attachment to the applicator drum, and pressed into contact with the adhesive side of the base layer. The dam patches may be attached to the applicator drum by a vacuum, which is selectively interrupted in order to release the cut dam patches from the applicator drum. Also, the backing material preferably has a base layer with a continuous, pressure sensitive adhesive side, and a cover layer that normally overlies the adhesive side, wherein the cover layer is separated from the base layer prior to the dam patches being pressed against the base layer.

The present invention further comtemplates positioning medicine-filled pads on the interior surfaces of the dam patches, and applying an imperforate, removable outer sheet over the medicine-filled pads to form sealed reservoirs in which the medicine-filled pads are retained. The removable outer sheet and cover layer are then cut into a plurality of individual compresses. The removable outer sheet is securely, yet detachably connected to the dam patch adjacent the marginal edge thereof to form the sealed reservoir. An absorbant cushion may be positioned over the exterior side of each of the dam patches, which extends past the marginal edge thereof, so that any excess medication which may seep around the dam patch is absorbed in the absorbant cushion. An imperforate shield is preferably applied over the external side of the absorbant cushion to protect the patient's clothing.

The present invention also contemplates a machine, which is capable of quickly and efficiently forming the compress base assemblies in accordance with the steps set forth above. The machine has a continuous feed operation, with a plurality of cutting dies that are carefully synchronized to insure smooth operation and maximum efficiency.

The above method and apparatus provide an arrangement for manufacturing compress base assemblies of the type that are particularly adapted to be used with topically applied medications. The compress base units are very strong and secure, and provide ready access to the dam patches, so that extra covering material is not required to be removed when the medicated pads are positioned on the dam patchs. Also, the adhesive layer on the backing material is at all times protected during the step of applying the medicine-carrying cushion, so that the compresses can be easily handled and processed, and will not leak when applied.

The medicine dispensing compresses, when finally assembled, provide medical personnel, and more importantly, the users themselves, with an easy-to-use method of medication application. The patient is not required to measure the proper dosage of medication, but merely applies a prescribed compress, which already contains an accurately premeasured dosage of medication. Because the compress is fully sealed in an imperforate material, the compress can be easily handled without danger of accidental misapplication of the medicine. A person merely strips away the imperforate outer sheet and the cover layer, and then directly adheres the compress to his skin. The compress is a self-contained, single unit, so that adhesive tape applicators and plastic film patches are not required. The compress allows for adhesion around its entire circumference, so as to prevent leakage. In addition to preventing leakage of medication out of the compress, the compress prevents the leakage of moisture into the medication reservoir, so that a user may shower, swim or bathe with the compress in place. The compress further provides an absorbant cushion for absorbing excess medication, should a faulty application of the compress to the user's skin result in some leakage around the dam patch. A shield over the absorbent cushion protects the user's clothing, without requiring any other protective materials.

These and other features, advantages and objects of the present invention will be further understood and appreciated by those skilled in the art by reference to the following written specification, claims and appended drawings.

BRIEF DESCRIPTION OF THE DRAWINGS

FIG. 1 is a front elevational view of a pharmaceutical packaging machine for compresses and the like embodying the present invention;

FIG. 4 is a rear elevational view of the compress machine;

FIG. 5 is a fragmentary, top plan view of a finished sheet of compress base assemblies fabricated in accordance with the present invention;

FIG. 6 is a fragmentary, sectional view of a finished sheet of base units taken along line VI—VI of FIG. 5, wherein the thickness of the various layers has been enlarged disproportionately to facilitate illustration;

FIG. 7 is a partially schematic, cross-sectional view of a completed compress fabricated in accordance with the present invention;

FIG. 8 is a cross-sectional view of the compress, shown affixed to a user's skin;

FIG. 9 is a perspective view of the compress, with portions thereof broken away to reveal internal construction;

FIG. 13 is a partially schematic, cross-sectional view of a cover liner offal removing portion of the compress machine.

DETAILED DESCRIPTION OF THE PREFERRED EMBODIMENT

For purposes of description herein, the terms "upper," "lower," "right," "left," "rear," "front," "vertical," "horizontal," and derivatives thereof shall relate to the invention as oriented in FIG. 1. However, it is to be understood that the invention may assume various alternative orientations and step sequences, except where expressly specified to the contrary.

Figure 3:
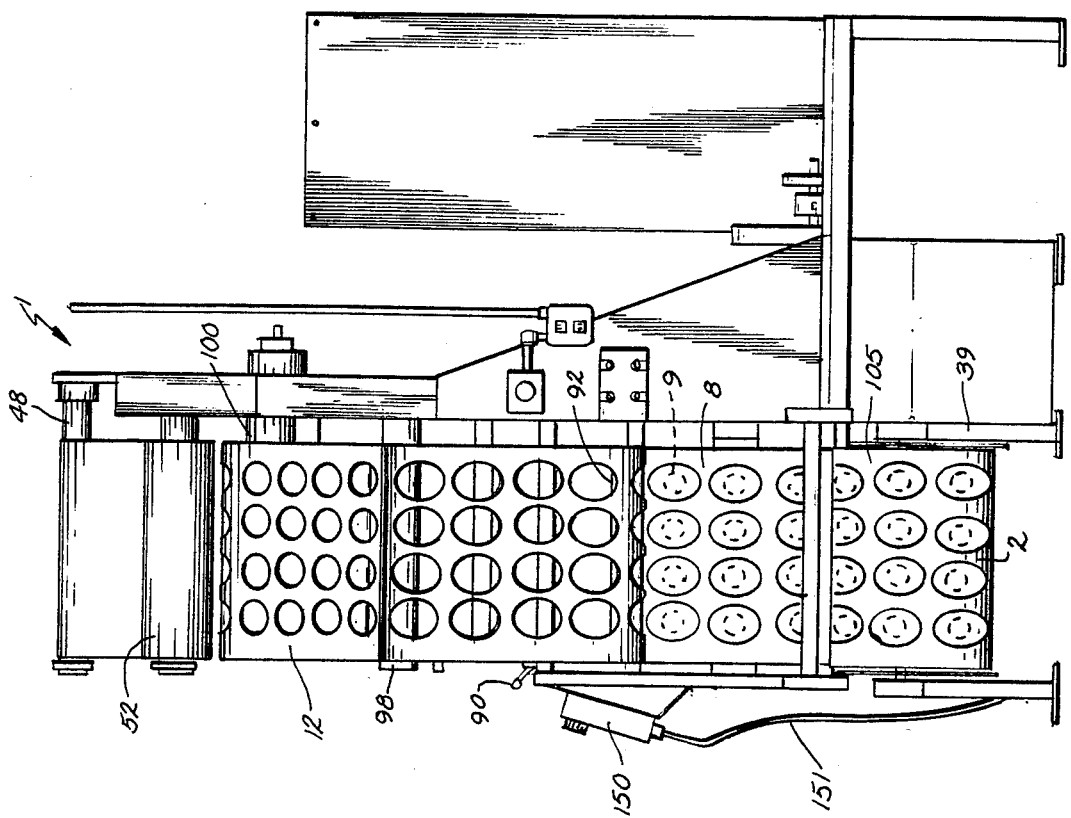
FIG. 3 is a side elevational view of the right-hand side of the compress machine.
Figure 2:
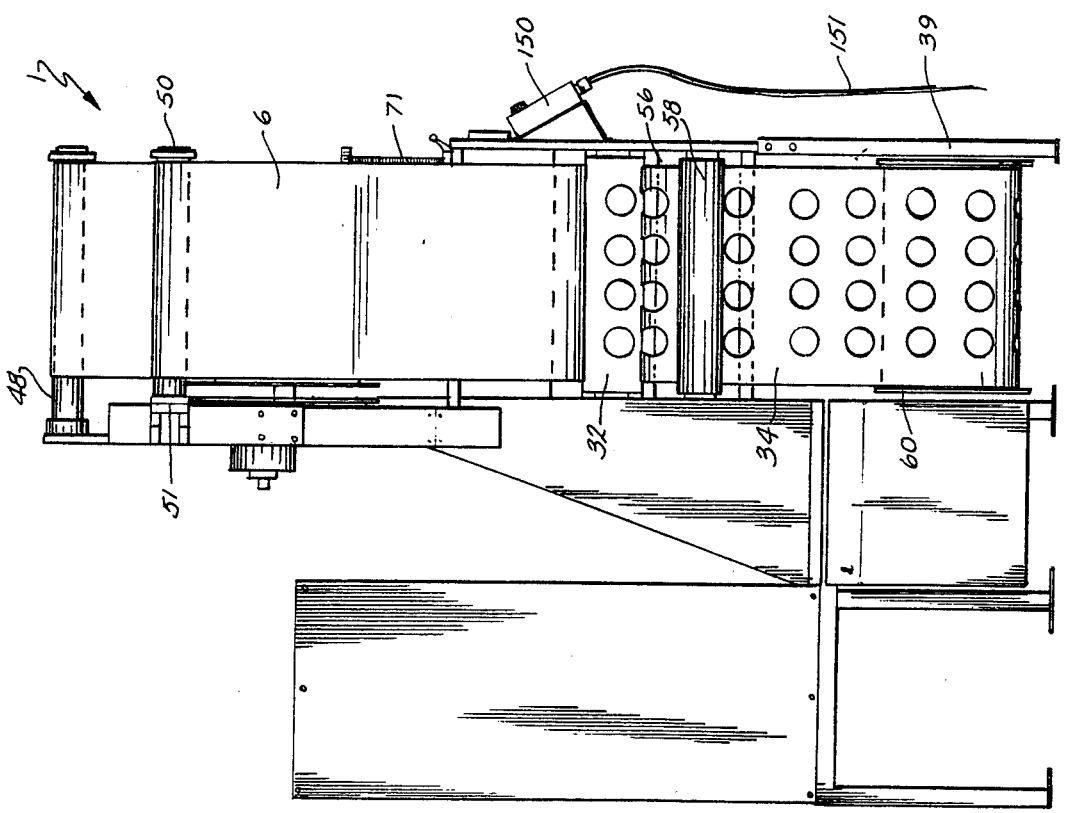
FIG. 2 is a side elevational view of the left-hand side of the compress machine.

In the preferred embodiment, a machine 1 (FIG. 1) is provided to manufacture base assemblies 2 (FIG. 6) for medicine dispensing bandages or compresses 3 (FIG. 7), and other similar articles. The machine 1, and associated fabricating method include using a web of substantially imperforate material 4 (FIG. 1), and a web of backing material 5 that has a base layer 6 with an adherent on one side 7 for attaching the compress 3 to the skin of a user. The backing material 5 also includes a cover layer 8, which normally overlies and protects the adhesive side 7 of base layer 6. A series of individual foil lids or dam patches 9 (FIG. 6) are cut from the web of imperforate material 4, and are applied to the adhesive side 7 of the base layer 6 in a preselected, spaced apart pattern. Machine 1 then applies the cover layer 8 to the adhesive side 7 of base layer 6, sandwiching dam patches 9 between base layer 6 and cover layer 8. Machine 1 cuts individual units 10 in base layer 6, with one of the dam patches 9 positioned within each of the base units 10. Apertures 11 are then cut into cover layer 8 in those portions overlying dam patches 9, in order to expose and access a portion of each dam patch 9 for placement of a medicated pad 15 thereon. Surrounding the individual base units 10 is an offal portion 12 (FIG. 3) of base layer 6, which the machine 1 removes from cover layer 8. The fully fabricated base assemblies 2 are conveniently carried together on cover layer 8 for final assembly. Machine 1 preferably includes a roller cutting die 30 (FIG. 11) which cuts the dam patches 9 from the web of imperforate dam patch material 4, and a vacuum operated applicator drum 32, that separates dam patches 9 from the surrounding offal portion 34 of the imperforate web 4. Applicator drum 32 then presses dam patches 9 into contact with the adhesive side 7 of base layer 6.

The medicine dispensing bandage or compress 3 described herein is best illustrated in FIGS. 7–9. However, it is to be understood that other compress designs and constructions may also be fabricated in accordance with the novel method and machine contemplated herein. In the illustrated structure, each compress 3 comprises a base assembly 2, a medicine-filled pad 15, and a removable outer sheet 16. As previously mentioned, each base assembly 2 (FIGS. 5 and 6) has a base layer 6, a dam patch 9, and a cover layer 8. Base layer 6 is constructed from a thin, flexible sheet of generally perforate, fibrous material, which is particularly adapted to conform readily to the skin of the user when applied thereto. The interior side 7 of the base layer 6 preferably has a preapplied, continuous coating of pressure sensitive, medical grade adhesive, of the type designed to stick to human skin. However, it is to be understood that a liquid adhesive or the like could be applied to the interior side 7 of base layer 6 as the backing web 5 is fed into the machine 1. The illustrated, individual base members or units 10, which are cut from the web of base material 6, have a generally ovate plan configuration, as best shown in FIG. 5. The base units 10 are positioned on the cover layer 8, in a mutually spaced apart relationship, as will be described in greater detail hereinafter.

In the illustrated example, dam patches 9 have a circular plan shape, and are constructed of a two-ply, imperforate material, comprising a foil side 17 constructed of aluminum or the like, and being oriented toward medicated pad 15 and a plastic side 18 bonded thereto, and oriented toward base unit 10. The plastic side 18 of dam patch 9 is adapted to stick securely to the adhesive side 7 of base unit 10, and the foil side 17 of dam patch 9 is designed to abuttingly support the medicated pad 15 thereon for extended periods of time without leakage, deterioration, or any other type of reaction that might effect the purity or integrity of the medication.

The release or cover layer 8 is constructed from a rather dense, imperforate material, with slick, impregnated surfaces which protect the adhesive side 7 of base layer 6, and can be easily peeled therefrom, as described in greater detail hereinbelow. Individual cover members or units 20 (FIGS. 7 and 9) are ultimately cut from cover layer 8 to form the compresses 3. Each of the illustrated cover units 20 has a substantially rectangular plan shape, with arcuately cut away corners 21 which expose the associated corners of the removable outer sheet 16 to facilitate grasping and removal of the outer sheet. In FIG. 5, the broken lines 23 illustrate the marginal edge of one of the individual compress units 3 which is eventually cut from the web of base assemblies. The cover units 20 are also split longitudinally along line 22, so that the cover layer 8 can be easily removed from the adhesive side 7 of the base layer 6 prior to the application of the compress 3 to the skin of the user. In this example, the pad apertures 11 are positioned in the geometric center of the associated cover layer member 20, such that the edge defining the apertures 11 lies wholly within the marginal edge of the adjacent dam patch 9. In other words, apertures 11 expose a continuous, imperforate central area of the dam patch foil side 17 on which the medicated pads 15 are supported.

The illustrated pads 15 comprise absorbant, sponge-like discs, which are adapted to hold a transdermally absorbed medication, such as nitroglycerin therein. The pads 15 have a diameter which is less than the diameter of the apertures 26, and associated exposed foil areas of the dam patches 9. During final assembly of the compresses 3, the medicated pads 15 are placed on the exposed foil surfaces 17 of the dam patches 9, and are centered within the associated cover member aperture 11.

The removable outer sheets 16 are constructed of an imperforate material, similar to the bonded foil and plastic film arrangement discussed above with respect to the dam patches 9. Each removable outer sheet 16 has a generally rectangular plan shape, which is substantially coextensive with the shape of the base layer units 10. The square corners of the removable outer sheets 16 are exposed by the arcuately cut away corners 21 of the underlying cover unit 20. The removable outer sheet 16 overlies the outermost surface of the cover unit 20, and is detachably adhered thereto by a heat seal, or the like, except at the interior of the dam patch 9, thereby forming a sealed chamber or reservoir 24 in which the medicated pad 15 is retained. An extra strong, annular bond line or protective seal 25 (FIG. 7) is provided between the removable outer sheet 16 and the dam patch 9, which extends continuously between the peripheral edge of the medicated pad 15 and the cover unit edge defining the aperture 11. Both heat and/or localized pressure can be used to form the annular seal 25, thereby making the interior of reservoir 24 both airtight and watertight.

The foil surface of the removable outer sheet 16 is oriented adjacent the foil side 17 of the dam patch 9, such that the interior of the reservoir 24 formed therebetween is completely foil lined for improved integrity.

In the compress 3 illustrated in FIGS. 7–9, a protective absorber or cushion 26 is provided on the outer side of the compress 3 to absorb any medication which might leak from the compress if it is improperly applied to the skin of the user, punctured, or otherwise inadvertently develops a leak. In this example, absorber 26 comprises two circular pads 27 constructed of gauze or the like, which are positioned overlying the exterior side 28 of base unit 10. Absorbant pads 27 are disposed mutually concentric, and have a diameter which is somewhat larger than the diameter of the dam patches 9. The peripheral edges of the absorbant pads 27 are attached to the exterior side 28 of base unit 10 at a location spaced radially outwardly of the peripheral edge of dam patch 9. When the compress 3 is applied to the user's skin, as shown in FIG. 8, any medication which might seep past the marginal edge of the dam patch 9 is absorbed into pads 27 through the outer periphery of the perforate base layer member 10.

An imperforate shield 29 extends over the exterior side of the absorber 26 to prevent any medication absorbed in pads 27 from coming in contact with and soiling the clothes of the user. Shield 29 comprises a thin layer of plastic film, having a circular plan shape. The diameter of shield 29 is slightly larger than the diameter of absorbant pads 27, such that the peripheral edge of shield 29 extends beyond that of the pads 27, and is connected with the base layer member 10 by suitable means, such as an adhesive, heat bonding, or the like. In the illustrated compress 3, shield 29 also retains absorbant pads 27 in place.

As best shown in FIG. 1, compress machine 1 includes a frame 39, and a housing 40 with a base 42 that supports the various elements of the machine. On the upper, left-hand side of housing 40 is a base layer feed support 44. Base layer feed support 44 is generally rectangular in shape, and includes a supply reel or drum 46 rotatably mounted near its base. Base layer supply drum 46 carries a continuous strip of backing material 5, which has base layer 6 and a liner or cover layer 8 adhered to the adhesive side 7 of base layer 6. Cover layer 8 allows base layer 6 to feed freely off drum 46. A clutch or rotational damper mechanism 47 (FIG. 4) is attached to supply drum 46, and prevents the drum from overspinning as the web 5 is payed from the drum, thereby maintaining tension in the base and cover layers 6 and 8 of the backing material 5 during processing. Rotatably mounted generally above and to the right of supply drum 46 on support 44 is a first idler roller 48. The cover layer 8 of backing material 5 is directed over the first idler roller 48 from supply drum 46. A second idler roller 50 is mounted on a horizontally extending arm portion 51 of support 44, at a location above and to the left of supply drum 46, as viewed in FIG. 1. The base layer 6 is directed over the second idler roller 50. Tension applied to the base layer 6 in a manner described below, pulls the backing material 5 off of supply drum 46. As the backing material is so dispensed from supply drum 46, the orientation of idler roller 48 pulls the cover layer 8 in an opposite direction from the base layer 6, thereby stripping apart or separating the two backing material layers, with the adhesive side 7 of the base layer 6 oriented away from the outer surface of idler roller 50. A take-up roller 52 is mounted on support 44, at a location below and to the right of idler roller 48, and winds up the cover layer 8 stripped from the backing material 5 into a roll for further processing, as will be discussed below. A clutched motor arrangement 53 (FIG. 4) powers take-up roller 52, and maintains tension on that part of the cover layer web 8 disposed between supply drum 46 and take-up roller 52.

A second supply reel or drum 54 is rotatably mounted on the lower portion of housing 40, and is adapted to carry a roll of imperforate foil material 4 thereon. Like backing supply drum 46, the foil supply drum 54 includes a rotational damper or brake to control the rotational speed of supply drum 54, and maintain tension in the foil web 4.

Figure 10:
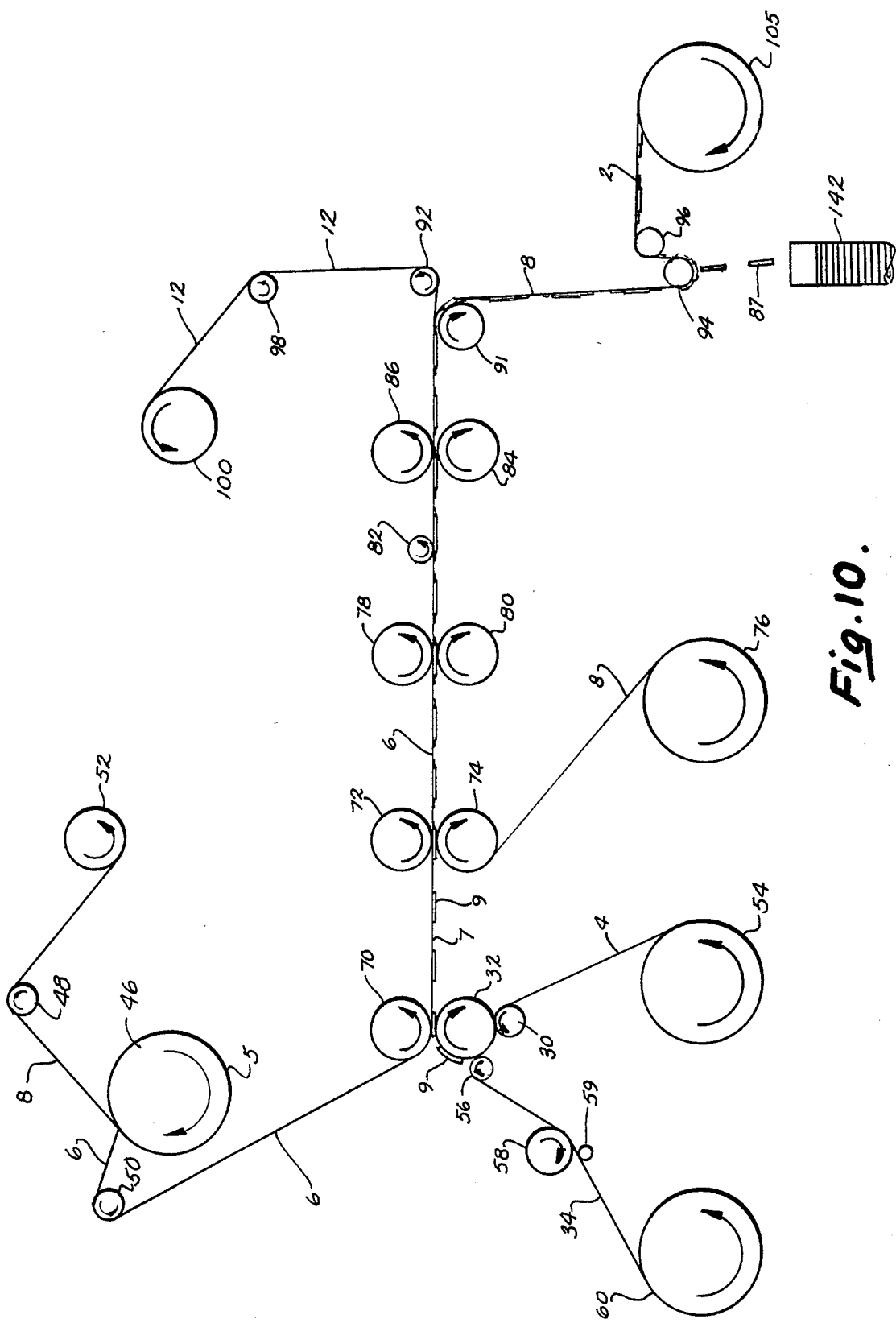
FIG. 10 is a schematic diagram of the method and machine embodying the present invention.
Figure 11:
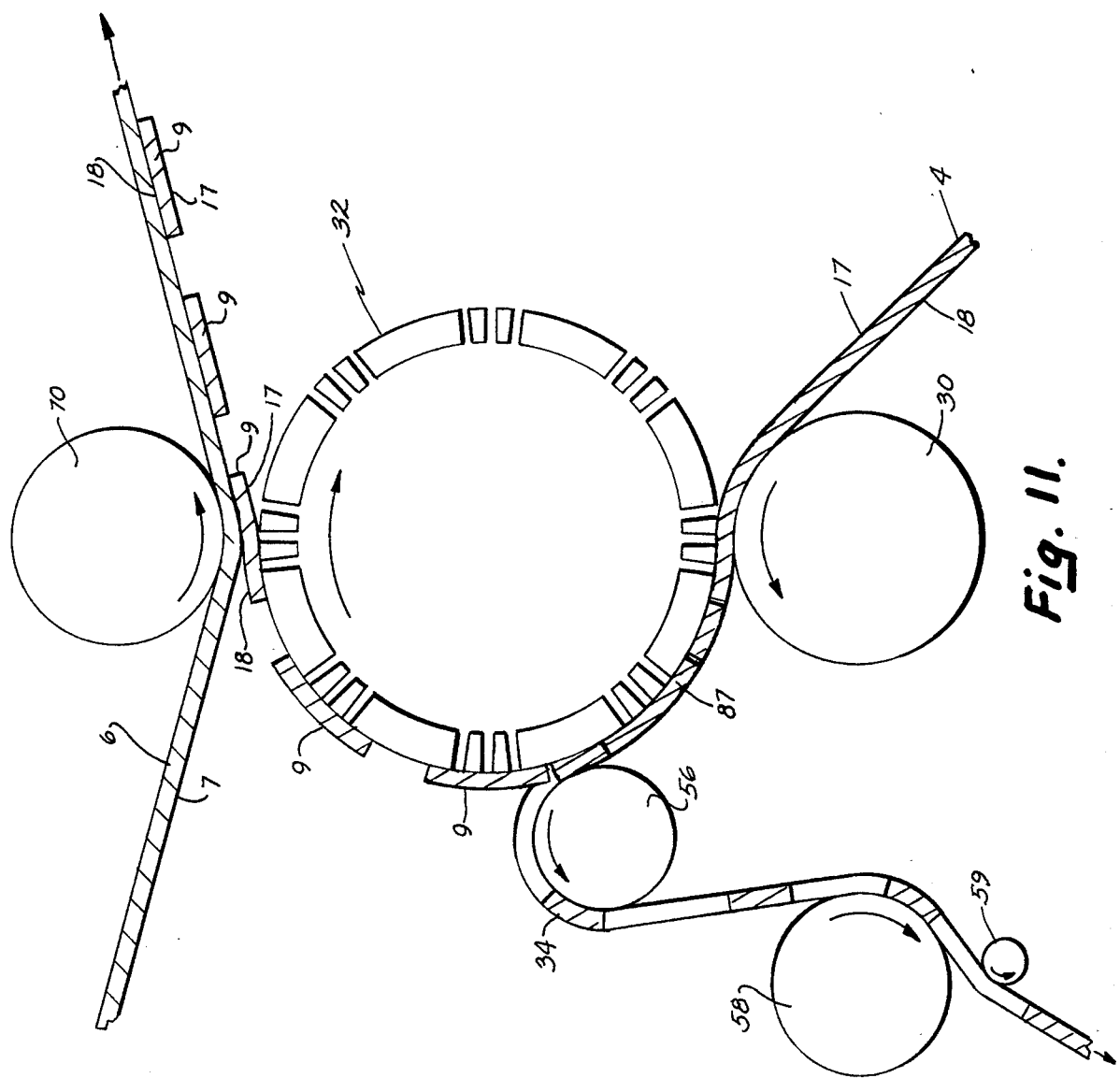
FIG. 11 is a fragmentary, cross-sectional view of an applicator drum portion of the compress machine.

A pair of mounting plates 55 are positioned on the front and back sides of the housing 40 at the left-hand side thereof, and are adapted to retain a plurality of rollers therebetween. Rotatably mounted between plates 55, and positioned above and to the left of foil web supply roller 54 is the cutting roller 30 (FIG. 11). Mounted slightly above and to the left of cutting roller 30 is a dam patch removal roller 56. Dam patch removal roller 56 has a diameter relatively small compared with idler rollers 48 and 50. Both cutting roller 30 and removal roller 56 are used in the forming of dam patches 9. Beneath and rotatably mounted to the left of dam patch removal roller 56 is an offset foil roller 58. An idler roller 59 is rotatably mounted between plates 55 at a location below, and slightly to the right of offset foil roller 58. Mounted beneath and to the left of offset roller 58 and idler roller 59 is foil offal take-up reel 60 (FIG. 10). Offset foil roller 58 and idler roller 59 are positioned in the path of web travel between dam patch removal roller 56 and foil offal take-up roller 60, so that proper tension is maintained in foil web 4 as it flows through machine 1. Foil web 4 travels upwardly from supply drum 54, between cutting roller 30 and anvil roller 32, around the top of dam patch removal roller 56, down under offset roller 58, and idler roller 59, and is collected on take-up roller 60. The rollers rotate in the directions indicatd by the various arrows shown in FIG. 10.

The patch applicator drum and anvil die 32 (FIG. 11) is located directly above cutting roller die 30 and slightly above and to the right of dam patch removal roller 56. Applicator drum 32 is a hollow, rotatably mounted cylinder, having a circumference which contacts the outer circumference of dam patch cutting die 30, and dam patch removal roller 56. The cutting roller die 30 has a plurality of rows of raised cutting edges (not shown), which mate with mating recesses 64 in applicator drum 32, so that the applicator drum also functions as an anvil roller. In this example, the cutting roller die 30 and mating applicator drum 32 are designed to cut four, circular dam patches 9, arranged laterally in line across the width of foil web 4.

Figure 12:
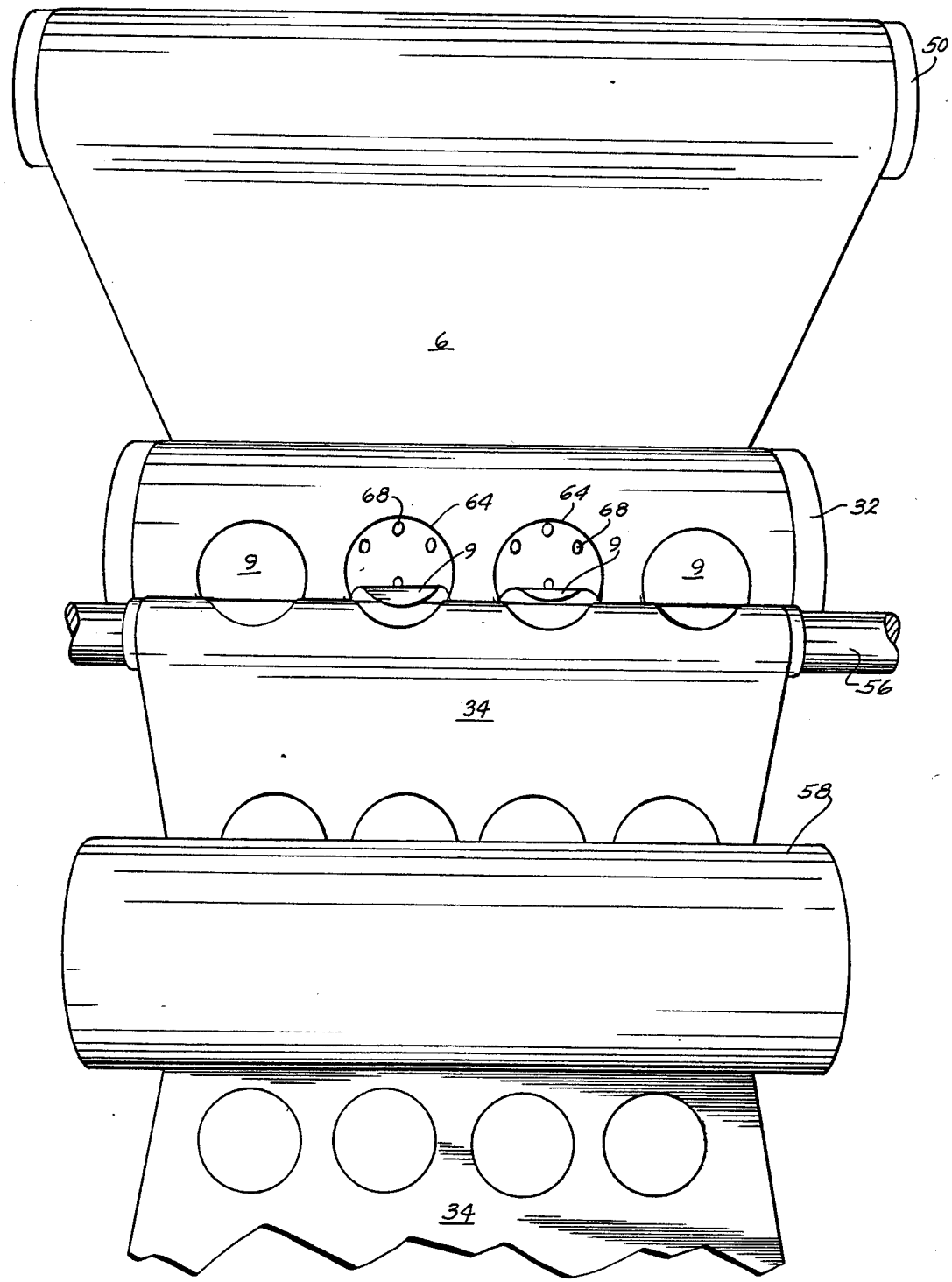
FIG. 12 is an end, perspective view of the rotating applicator drum of the compress machine.

Within each anvil die surface 64 on applicator drum 32, a plurality of vacuum apertures 68 (FIGS. 11 and 12) are provided, which extend through the wall of the applicator drum, and communicate with the interior of drum 32. As shown in FIG. 12, the illustrated vacuum apertures 68 are arranged in a circular configuration within each of the circular anvil die surfaces 64 on applicator drum 32. It is to be noted, that for illustrative purposes the center two dam patches 9 are pulled away from the peripheral surface of the applicator drum 32 to expose some of the vacuum apertures 68. A hose 65 (FIG. 1), with swivel fitting 66 attached to the axle of applicator drum 32, communicates the interior of the applicator drum with a conventional source of vacuum. The illustrated machine 1 includes a motor 67 (FIG. 4), vacuum pump 68 and vented reservoir 69 mounted at the rear of the machine to supply vacuum to the interior of the applicator drum 32. As foil web 4 (FIG. 11) passes between cutting roller die 30 and applicator drum 32, row of dam patches 9 are cut in foil web 4. The vacuum communicated through the vacuum apertures 68, draws the cut dam patches 9 against the outer peripheral surface of applicator drum 32. As the cut foil web 4 passes over the severe bend induced by removal roller 56, the foil web 4 is curled backwardly around removal roller 56. This bending motion causes the dam patches 9 to peel cleanly away from the foil web 4. The relative position of dam patch removal roller 56 and applicator drum 32 is preferably adjustable to optimize the efficiency of the dam patch removal operation. The tangent angle between applicator drum 32 and roller 56 is generally, preferably greater than 45 degrees to insure proper separation of the dam patches 9 from the foil web 4, and correct insertion of the dam patches 9 between rollers 32 and 70. However, there are several variables such as the precise characteristics, such as stiffness, of the material being cut, roll set or curve, humidity, machine speed, etc, which affect dam patch separation. It is therefore quite advantageous to adjustably mount the applicator drum 32 and mating roller 56 to accommodate for such variables. Proper adjustment between drum 32 and roller 56 causes the cut dam patches 9 to stick securely to drum 32 until applied to the adhesive side 7 of base layer 6. The foil offal 34 is conveyed away and collected on drum 60. The dam patches 9 are held on the peripheral surface of applicator drum 32 by the vacuum induced through apertures 68.

Located directly above applicator drum 32 is a base layer pressure roll 70 (FIG. 11). Base layer pressure roll 70 is spaced apart from applicator drum 32 a preselected distance, so that base layer 6 and dam patches 9 are pressed securely into contact with each other when they pass between roller 70 and applicator drum 32. Adjustment knobs 71 (FIG. 1) are mounted on the housing plates 55, and adjust the spacing between applicator drum 32 and roller 70 by a conventional arrangement.

After the cut dam patches 9 are bodily removed from the foil web 4, applicator drum 32 transports the cut dam patches 9 to pressure roller 70, and presses the dam patches 9 into contact with the adhesive side 7 of base layer 6. The vacuum provided through apertures 68 is then interrupted, so as to release the dam patches 9 from the peripheral surface of applicator drum 32.

Rotatably mounted downstream of applicator drum 32 are a pair of cover layer applying rollers 72 and 74 (FIG. 10). A cover layer feed roller 76 is rotatably mounted beneath cover layer applying rollers 72 and 74, and carries a continuous sheet of cover layer or liner material 8 thereon. Preferably, the cover layer take-up roller 52 is interchangeable with the cover layer feed roller 76, so that the cover layer 8 stripped from the backing material 5 prior to the application of the dam patches 9 to the base layer 6 can be reused to cover the adhesive side 7 of base layer 6, after the dam patches 9 have been applied. The cover layer 8 is payed off of feed roller 76, and is threaded between the cover layer applying rollers 72 and 74. The base layer web 6, with adhered dam patches 9 and cover layer 8, is also fed between cover layer applying rollers 72 and 74, such that the cover layer 8 is pressed firmly against the exposed portions of the adhesive side 7 of base layer 6. Adjustment knobs 77 (FIG. 1) are mounted on housing plates 55, and adjust the pressure between rollers 72 and 74 in a conventional fashion.

A pair of base layer cutting dies 78 and 80 are rotatably mounted downstream of cover layer applying rollers 72 and 74. Spaced around the circumference of cutting die 78 are rows of raised cutting surfaces that are oval in shape, which correspond with the shape of the base units 10. The cutting surfaces on cutting die 78 are aligned to correspond with mating anvil surfaces on die 80, and are positioned to cut oval base units 10 in the base layer 6 that are centered over the foil dam patches 9. Roller dies 78 and 80 are spaced apart a predetermined distance, so that the die surface on cutting die 78 cuts through only the base layer 6, and does not penetrate into cover layer 8. Adjustment knobs 81 (FIG. 1), are mounted on housing plates 55, and adjust the spacing between roller dies 78 and 80 in a conventional fashion.

An idler roller 82 (FIG. 10) is positioned downstream of roller dies 78 and 80, and changes the direction of web travel into the next machine station, as described below.

An access aperture cutting die 84 (FIG. 10) and mating anvil roller 86 are located downstream of idler roller 82, and are generally parallel with roller pairs 72 and 74 and 78 and 80. Aperture cutting die 84 is located directly beneath mating anvil roller 86, and has spaced about its circumference rows of raised circular die surfaces. The die surfaces on aperture cutting die 84 are rotationally aligned with the die surfaces on pressure roller pairs 72 and 74 and 78 and 80 for continuous, cutting operations. The mating die surfaces are spaced about the circumference of rollers 84 and 86, so that the access apertures 11 (FIG. 6) are cut into the cover layer 8 at each foil dam patch 9, thereby forming circular offal discs 87 that are ultimately removed from the cover layer to expose the foil side 17 of the dam patches 9. Also located on roller dies 84 and 86 are cutting surfaces for cutting four tear-away slits 22 (FIG. 5), and corner apertures 89 in cover layer 8. Tear-away slits 22 are straight cuts which run the length of cover layer 8, and join dam apertures 11 along each column of the base units 10. Corner apertures 89 are circular in shape, and are located at each corner of the base units 10 to form the cut away corners 21, as previously described. Aperture cutting die 84 and mating anvil roller 86 are spaced apart a predetermined distance, so that the die surfaces on cutting die 84 only cut through cover layer 8, and do not penetrate into either the foil dam patches 9 or the base layer 6. Adjustment knobs 90 (FIG. 1) are located on housing plates 55a, and control the separation between dies 84 and 86 by conventional means.

Located downstream of aperture cutting dies 84 and 86 is a stripper roller 91 (FIG. 10), which separates base layer offal 12 from the base assemblies 2. Located downstream and above separator roller 91 is a mating stripper roller 92 for the base layer offal 12. Located beneath stripper roller 92 are a pair of offset rollers 94 and 96. As the continuous sheet of cover layer 8, with foil dam patches 9 and cut base layer 6 come off roller 91, the base layer offal 12 passes over and around stripper roller 92, while the remainder of the assembly travels downwardly to offset rollers 94 and 96. Base layer offal collecting drum 100 is rotatably mounted on an upstanding bracket 102 (FIG. 1) of machine frame 39, and is rotated by a clutched drive mechanism 103 (FIG. 4).

Offset rollers 94 and 96 have a relatively small diameter, and are positioned so that cover layer 8, with base assemblies 2 thereon, makes a severe bend as it passes around upstream roller 94. Due to this severe bend, the circular plugs 87 and corner discs 89 cut in cover layer 8 are peeled or curled out of the cover layer 8, as best shown in FIG. 13. Positioned beneath offset roller 94 is a vacuum chute 105, which helps remove the offal plugs 87 and corner discs 89 from cover sheet 8, and then transports the same to a collection area for disposal. Four sponge rubber rings or bands (not shown) can be positioned on roller 92 in line with the longitudinal axes of the compress base assemblies 2 to help strip the circular corner discs 89 from the cover layer 8. Normally, the corner discs 89 so removed will stick to the adhesive side 7 of the base layer offal 12, and roll up on drum 100. Also, a special stripper roller (not shown) with resiliently mounted ejection spheres to positively punch the corner discs 89 out of the cover layer 8 can be mounted between rollers 91 and 94 to assist in removing the cover layer offal. Alternatively, a separate station may be provided for manually removing discs 87 and 89.

A final take-up reel or drum 105 is positioned downstream of offset rollers 94 and 96, and winds the finished web of base assemblies 2 into a roll or bolt. In this example, the finished web is wound with the apertured cover layer 8 and dam patches 9 oriented inwardly. A clutched drive (not shown) rotates drum 105, and maintains tension on the web. The illustrated take-up drum 105 is supported on a pivotal arm arrangement 106, which permits the operator to swing drum 105 outwardly when filled onto a pallet, or the like to facilitate removing the filled reel, and replacing it with an empty spool.

As best illustrated in FIG. 4, a drive mechanism 110 is positioned at the rear of machine 1, and is adapted to rotate the various cutter/pressure rollers and take-up drums in a synchronized fashion through a mechanical transmission 111. Drive mechanism 110 includes a conventional electric motor 112 mounted to machine base 113, and is adapted to drive two separate gear clusters 114 and 115 located on the left and right-hand sides respectively of the machine frame 39, as viewed from the rear in FIG. 4. The right-hand gear cluster 115 includes a central gear wheel 116, mounted in pillow blocks 117, and driven by motor 112 through a cleated, flexible drive belt 118. Gear wheel 116 in turn drives a main drive shaft 119, and three mutually entrained spur gears 120, 121 and 122. Spur gears 120–122 are connected with and drive roller pairs 30 and 32, 72 and 74, and 78 and 80 respectively. The clutched gear box arrangement 53 for cover layer take-up roller 52 is also driven from drive shaft 119 through a flexible drive belt 123. A spring loaded idler pulley 123a controls the tension in drive belt 123. A second drive belt 124 connects clutched gear box 53 with the input pulley 125 of cover layer take-up reel 52. Drive shaft 119 also provides power to the foil offal take-up roller 60 through a mechanical, clutch drive mechanism (not shown).

The left-hand gear cluster 114 includes a central gear wheel 130 rotatably mounted on the machine frame by pillow blocks 131. Gear wheel 130 is also driven by motor 112 through a flexible, cleated drive belt 132. Gear wheel 130 in turn rotates central drive shaft 133, and three associated spur gears 134, 135 and 136. Gears 134–136 in turn drive cutters/pressure rollers 84 and 85. The clutched gear box 103 for the base layer offal take-up drum 102 is also driven from central drive shaft 133 by a flexible drive belt 137. A spring loaded idler pulley 137a controls the tension in drive belt 137. The output shaft of clutched gear box 103 is in turn connected with the input pulley 138 of take-up drum 100 by a flexible drive belt 139. The take-up drum 105 on which the assembled base units are collected is also driven by central drive shaft 133 through a conventional, clutch transmission (not shown).

The driven pairs of rollers 30 and 32, 72 and 74, 78 and 80 and 84 and 86 are rotated in a synchronous fashion to achieve continuous operation. Tension rollers (not shown) are positioned throughout the path of web travel, and include conventional sensors which detect the web tension. An electrical control panel 140 houses automatic switches, which are connected with the web tension sensors, and adjust die roller speed accordingly to insure proper sequencing between the various roller die stations.

Another feature of the machine 1 which is provided to properly synchronize the various roller die stations is illustrated in FIG. 5. If the die rollers are not in precise synchronization, the web will be stretched, and the various parts of the base assembly (i.e., dam patches 9, base units 10, cover units 20, apertures 11, etc.) will not register correctly. The second pair of roller dies 72 and 74 include mating portions to periodically cut or scribe an aperture 145 along one side of the assembled base and cover layers 6 and 8. The indexing apertures 145 are therefore spaced longitudinally apart a predetermined distance. The third pair of roller dies 78 and 80 also include mating portions which periodically cut or scribe indexing apertures 146 along the same side of the web as indexing apetures 145. In the present example, the second indexing apertures 145 are slightly larger than the first indexing apertures 145. The indexing portions of die pairs 72 and 74 and 78 and 80 are positioned such that when the die pairs are in precise synchronization, the smaller indexing apertures 146 will fall into the exact center of the larger indexing apertures 145. When the indexing apertures 145 and 146 are not in precise alignment, the web tension and/or roller die pressure must be adjusted to reestablish proper sequencing between the various roller die stations. A spring loaded idler pulley 137a controls the tension in drive belt 137.

OPERATION

With reference to FIG. 10, machine 1 operates in the following manner. A roll of backing material 5 is mounted on supply drum 46, with the base layer 6 oriented on the outside surface of the roll. The cover layer 8 prevents the various plies of the roll from sticking together, so that the backing material 5 will dispense freely off of drum 46. A length of backing material 5 is manually pulled off of supply drum 46 to thread through the machine 1 for initial setup. The cover layer 8 is manually stripped or separated from the base layer 6 on the free end of the backing material web 5. The free end of the cover layer 8 is passed over and around idler roll 48, and is then secured or anchored to take-up roller 52. The adherent side 7 of base layer 6 is disposed upwardly as base layer 6 pays off of supply drum 46. The free end of base layer 6 is passed over and around idler roller 50, so that the non-adherent side of the base layer 6 contacts idler roller 50. The base layer 6 is then threaded between roller pairs 32 and 70, 72 and 74, 78 and 80; under idler roller 82, between roller pair 84 and 86, over idler roller 91, under roller 92, over idler roller 98, and then achored to take-up drum 100. Since take-up roller 52 and rollers 32 and 70 are driven, the backing material 5 is continually pulled off of supply drum 46, and the cover layer 8 is continuously stripped from the base layer 6 between idler rollers 48 and 50, and wound onto take-up roller 52.

A roll of foil material 4 is mounted on supply roller 54. A length of foil material is manually pulled off of supply roller 54, and the free end is inserted between cutter roller 30 and applicator drum 32, around the lower, left-hand quadrant of applicator drum 32 between roller 56, over roller 56, under roller 58, and over roller 59, and then anchored to the foil offal take-up drum 60. As foil web 4 passes between cutter roller die 30 and anvil/applicator drum 32, the circular dam patches 9 are cut. As best illustrated in FIG. 11, the vacuum applied to the hollow interior of applicator drum 32 holds the foil web 4 securely against the outer peripheral surface of the drum 32. As the foil web 4 passes over stripper roller 56, the offal portion 34 of foil web 4 is stripped away from the outer peripheral surface of applicator drum 32. The circular dam patches 9 are retained or held on the outer surface of applicator drum 32 by the vacuum. The foil offal 34 then passes over rollers 58 and 59, and is collected on take-up drum 60.

The cut dam patches 9 which are held on the outer surface of applicator drum 32 by vacuum are then pressed onto the adhesive surface 7 of the base layer web 6 by pressure roller 70 at the upper side of applicator drum 32. The interior vacuum in applicator drum 32 is then interrupted, so that the cut dam patches 9 are released from applicator drum 32, and carried in rows on the base layer web 6.

A roll of cover layer material 8 (FIG. 10) is mounted on supply roller 74. A length of the cover layer material 8 is drawn off of roll 76, and inserted between rollers 72 and 74, 78 and 80, under roller 82, between rollers 84 and 86, over roller 91, over rollers 94 and 96, and then anchored to take-up drum 105. After cover layer 8 has been threaded through the various rollers described above, machine 1 is ready for operation. As will be apparent to those skilled in the art, machine 1 can be set up in many different ways to facilitate fabricating various styles of compresses, and other similar articles.

With reference to FIG. 10, as the base layer web 6, with cut dam patches 9 thereon is conveyed between rollers 72 and 76, the cover layer web 8 is pressed onto the exposed portions of the adhesive side 7 of the base layer, such that the dam patches 9 are sandwiched between continuous sheets of base layer material 6 and cover layer material 8.

The sandwiched assembly then passes between cutting rollers 78 and 80, wherein roller die 78 cuts the individual base units 10 in the web of base material 6. A base unit 10 is cut centered over each dam patch 9. Base layer 6 is thusly divided into individual units with a surrounding continuous sheet of offal 12.

The cut base layer 6, with dam patches 9 and continuous cover layer 8 then pass under idler roller 82, and is conveyed to and between access aperture cutting roller dies 84 and 86. As the continuous sheet passes between cutting dies 84 and 86, roller die 84 cuts access apertures 11, tear-away slits 22, and corner apertures 89 into and through cover layer 8. The cover layer 8 therefore comprises a continuous sheet, which as best illustrated in FIG. 5, has four tear-away slits 22 extending along its length, wherein each slit runs under the center of a column of base assembly units 2. Corner apertures 89 are positioned at the corners of the base units 10, and form the arcuate corners 21 thereof when the compresses are assembled.

As the cut base layer 6, with dam patches 9 and cut cover layer 8 pass over separator roller 91, the offal portion 12 of base layer 6 is stripped off of the cover layer 8. The offal portion of the base layer material extends over idler rollers 92 and 98, and is collected on take-up roller 100.

As the fabricated cover layer web 5 with dam patches 9 and assembled base units 10 thereon pass over offset rollers 94 and 96, the severe bend of the web causes the circular disc 87 forming apertures 11 and corner discs 89 to peel away from the remainder of the cover layer 8, as shown in FIG. 13. Vacuum tube 142 is positioned directly beneath the lowermost offset roller 94, and applies a vacuum to the adjacent surface of cover layer 6. This vacuum assists in peeling the offal plugs 87 and corner aperture plugs 89 from the cover layer 8, and collecting the same for disposal. Since the circular aperture discs 87 are in contact only with the foil dam patches 9, they do not adhere to the base layer 6, and can be readily removed. In a like manner, corner aperture plugs 89 are located in areas of cover layer 8 which have had adhesive base layer 6 removed, such that plugs 89 can also be easily removed from cover layer 8.

The continuous sheet of completed base assemblies 2 are collected on take-up drum 105 to facilitate further process, as previously described.

In use, the user grasps the corner portion of the removable outer sheet 16 which extends over the cut away corner 21 of cover unit 20. Outer sheet 16 is then peeled away from the cover unit 20, thereby exposing medicated pad 15. The cover layer 20 is then peeled off of the compress unit, along tear-away slit 22, thereby exposing the adhesive side 7 of the compress unit. Compress 3 is then pressed against the application area of the user, so that it adheres securely to his skin. The medication is absorbed transdermally into the user's circulatory system.

In the foregoing description it will be readily appreciated by those skilled in the art that modifications may be made to the invention without departing from the concepts disclosed herein. Such modifications are to be considered as included in the following claims, unless these claims by their language expressly state otherwise.

The embodiments of the invention in which an exclusive property or privilege are claimed is defined as follows:

1. A method for making base assemblies for medicine dispensing compresses and the like, comprising:
   providing a web of substantially imperforate material, and a web of backing material, said backing material having a base layer with one adhesive side, and a cover layer normally overlying the adhesive side of the base layer;
   separating the cover layer from the base layer of the backing material;
   cutting a plurality of individual dam patches from the web of imperforate material, said dam patches each having a preselected shape, interior and exterior surfaces, and a marginal edge;
   applying the dam patches to the adhesive side of the base layer in a preselected pattern, with the interior surfaces of the dam patches oriented outwardly;
   applying the cover layer to the remaining exposed portion of the adhesive side of the base layer, such that the dam patches are sandwiched between the base layer and the cover layer;
   cutting a plurality of individual base units in the base layer, with one of the dam patches positioned within each of the base units, that portion of the base layer disposed outside of the base units defining an offal portion of the base layer;
   cutting a plurality of apertures in the cover layer to selectively access a portion of the interior surface of each of the dam patches, said apertures being located at each of those areas of the cover layer overlying the dam patches, and being positioned wholly within the marginal edge of the associated adjacent dam patch to facilitate centering medicine-filled pads on the interior surface of the dam patches; and
   removing the offal portion of the base layer from the cover layer, thereby forming a plurality of fabricated base assemblies for the compresses, which are carried together on the cover layer for final assembly.

2. A method as set forth in claim 1, wherein said dam patch cutting and applying steps comprise:
   roller die cutting the dam patches in the web of imperforate material;
   temporarily attaching the dam patches to a rotating applicator drum;

separating an offal portion of the imperforate material from the dam patches after the dam patches are attached to the applicator drum;

releasing the attachment of the dam patches to the applicator drum after the associated offal portion of the imperforate material has been separated therefrom; and pressing the dam patches into contact with said adhesive side of the base layer.

3. A method as set forth in claim 2, wherein:

said dam patch applying step comprises applying a vacuum between the applicator drum and the interior side of the dam patches; and said dam patch releasing step comprises interrupting the vacuum between the applicator drum and the interior side of the dam patches.

4. A method as set forth in claim 3, wherein:

said imperforate material offal portion separating step comprises passing the offal portion of the imperforate material over a first roller positioned adjacent the applicator drum in order to bend the offal portion away from the drum, thereby urging the dam patches out of the offal portion of the imperforate material.

5. A method as set forth in claim 4, wherein:

said base layer cutting step comprises roller die cutting through the other side of the base layer.

6. A method as set forth in claim 5 wherein said aperture cutting step comprises:

roller die cutting through the interior side of the cover layer, and positioning the apertures wholly within the marginal edge of the associated adjacent dam patch to avoid adhering the base layer to the cutout offal portion of the cover layer; and passing the cover layer over second and third, mutually offset rollers, with the cover layer positioned outermost as the cover layer passes over a downstreammost one of the rollers, thereby urging the cutout offal portions in the cover layer to separate from the cover layer.

7. A method as set forth in claim 6, wherein said aperture cutting step further comprises:

applying a vacuum to the offal portions of the cover layer as the same passes over the downstream roller.

8. A method as set forth in claim 7, including:

rolling the assembled base units into a bolt to facilitate final assembly.

9. A method as set forth in claim 8, wherein:

said cover layer separating step comprises winding the separated cover layer into a roll for reuse in applying the cover layer to the adhesive side of the base layer after the dam patches are applied to the base layer.

10. A method as set forth in claim 9, wherein:

said dam patch releasing step further comprises adjusting the relative position of mating roller dies cutting the dam patches.

11. A method as set forth in claim 10, wherein said cover layer separating step further comprises:

paying the backing material from a roll thereof;

pulling the cover layer in one direction before winding the separated cover layer into a roll; and pulling the base layer in an opposite direction before feeding the base layer into mating roller dies.

12. A method as set forth in claim 11, including:

cutting slits through the cover layer at each row of the base assemblies to facilitate application of the compresses.

13. A method as set forth in claim 12, including:

cutting apertures through the cover layer at adjoining corners of the base units to facilitate application of the compresses.

14. A method as set forth in claim 1, wherein:

said perforate layer cutting step comprises roller die cutting through the other side of the base layer.

15. A method as set forth in claim 1 wherein said aperture cutting step comprises:

roller die cutting through the interior side of the cover layer, and positioning the apertures wholly within the marginal edge of the associated adjacent dam patch to avoid adhering said base layer to the cutout offal portions of the cover layer; and passing the cover layer over second and third, mutually offset rollers, with the cover layer positioned outermost as it passes over the downstream one of the rollers, thereby urging the cutout offal portions of the cover layer to separate from the cover layer.

16. A method as set forth in claim 1, including:

rolling the assembled base units into a bolt to facilitate final assembly.

17. A method as set forth in claim 1, wherein:

said cover layer separating step comprises winding the separated cover layer into a roll for reuse in applying the cover layer to the adhesive side of the base layer after the dam patches are applied to the base layer.

18. A method as set forth in claim 1, wherein:

said dam patch releasing step comprises adjusting the relative position of mating roller dies cutting the dam patches.

19. A method as set forth in claim 1, wherein said cover layer separating step comprises:

paying the backing material from a roll thereof;

pulling the cover layer in one direction before winding the separated cover layer into a roll; and pulling the base layer in an opposite direction before feeding the base layer into mating roller dies.

20. A method as set forth in claim 1, including:

cutting slits through the cover layer at each row of the base assemblies to facilitate application of the compresses.

21. A method as set forth in claim 1, including:

cutting apertures through the cover layer at adjoining corners of the base units to facilitate application of the compresses.

22. A method for making medicine dispensing compresses and the like, comprising:

providing a web of substantially imperforate material, and a web of backing material, said backing material having a base layer with one adhesive side, and a cover layer normally overlying the adhesive side of the base layer;

separating the cover layer from the base layer of the backing material;

cutting a plurality of individual dam patches from the web of imperforate material, said dam patches each having a preselected shape, interior and exterior surfaces, and a marginal edge;

applying the dam patches to the remaining exposed portion of the adhesive side of the base layer in a preselected pattern, with the interior surfaces of the dam patches oriented outwardly;

applying the cover layer to the adhesive side of the base layer, such that the dam patches are sandwiched between the base layer and the cover layer;

cutting a plurality of individual base units in the base layer, with one of the dam patches positioned within each of the base units, that portion of the base layer disposed outside of the base units defining an offal portion of the base layer;

cutting a plurality of apertures in the cover layer to selectively access a portion of the interior surface of each of the dam patches, said apertures being located at each of those areas of the cover layer overlying the dam patches, and being positioned wholly within the marginal edge of the associated adjacent dam patch to facilitate centering medicine-filled pads on the interior surface of the dam patches;

removing the offal portion of the base layer from the cover layer;

positioning medicine-filled pads on the interior surfaces of the dam patches;

applying an imperforate, removable outer sheet over the medicine-filled pads to form sealed reservoirs in which the medicine-filled pads are retained; and cutting the removable outer sheet and the cover layer into a plurality of individual compresses.

23. A method as set forth in claim 22, wherein:

said removable outer sheet applying step includes detachably connecting the outer sheet to each of the dam patches along a line extending adjacent the marginal edge of the exposed access portion of the dam patch.

24. A method as set forth in claim 23, including:

detachably adhering the cover layer to the overlying portion of the removable outer sheet.

25. A method as set forth in claim 24, including:

positioning an absorbent cushion over the exterior side of each of the dam patches, and connecting each cushion with the other side of the perforate base layer along a line spaced outwardly of the marginal edge of the associate dam patch, whereby excess medication is absorbed into the cushion.

26. A method as set forth in claim 25, including:

applying an imperforate shield over the exterior side of the absorbent cushion to prevent medication from soiling the clothing of the user.

27. A method for making base assemblies for medicine dispensing compresses and the like, comprising:

providing a web of substantially imperforate material, and a web of backing material, said backing material having a base layer;

cutting a plurality of individual dam patches from the web of imperforate material, said dam patches each having a preselected shape, interior and exterior surfaces, and a marginal edge;

adhering the dam patches to one side of the base layer in a preselected pattern, with the interior surfaces of the dam patches oriented outwardly;

adhering a cover layer to the remaining exposed portion of the one side of the base layer, such that the dam patches are sandwiched between the base layer and the cover layer;

cutting a plurality of individual base units in the base layer, with one of the dam patches positioned within each of the base units, that portion of the base layer disposed outside of the base units defining an offal portion of the base layer;

cutting a plurality of apertures in the cover layer to selectively access a portion of the interior surface of each of the dam patches, said apertures being located at each of those areas of the cover layer overlying the dam patches, and being wholly within the marginal edge of the associated adjacent dam patch to facilitate centering medicine-filled pads on the interior surface of the dam patches;

removing the offal portion of the base layer from the cover layer, thereby forming a plurality of fabricated base assemblies for the compresses, which are carried together on the cover layer for final assembly.

28. A method as set forth in claim 27, wherein said dam patch adhering step comprises:

providing the one side of the base layer with a coating of pressure sensitive adhesive, and a cover layer normally overlying the adhesive side of the base layer;

separating the cover layer from the base layer prior to adhering the dam patches thereto; and pressing the dam patches into contact with the adhesive side of the base layer.

29. A method as set forth in claim 28, wherein said cover layer adhering step comprises:

pressing the cover layer into contact with the remaining exposed portion of the adhesive side of the base layer.

* * * * *